(12) United States Patent
Hsieh et al.

(10) Patent No.: US 6,535,572 B2
(45) Date of Patent: Mar. 18, 2003

(54) METHODS AND APPARATUS FOR COMPENSATING COMPUTED TOMOGRAPHIC CHANNEL GANGING ARTIFACTS

(75) Inventors: Jiang Hsieh, Brookfield, WI (US); Jianying Li, New Berlin, WI (US); Thomas L. Toth, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 43 days.

(21) Appl. No.: 09/882,770

(22) Filed: Jun. 15, 2001

(65) Prior Publication Data

US 2003/0002617 A1 Jan. 2, 2003

(51) Int. Cl.[7] .................................................. A61B 6/03
(52) U.S. Cl. .............................................. 378/19; 378/4
(58) Field of Search ........................... 378/4, 8, 15, 19, 378/99

(56) References Cited

U.S. PATENT DOCUMENTS

| | | |
|---|---|---|
| 4,361,901 A | 11/1982 | Daniels et al. |
| 5,131,021 A | 7/1992 | Gard et al. |
| 5,732,118 A | 3/1998 | Hsieh |
| 5,907,593 A | 5/1999 | Hsieh et al. |
| 5,974,109 A | 10/1999 | Hsieh |
| 6,061,419 A | 5/2000 | Hsieh et al. |
| 6,075,835 A | 6/2000 | Acharya et al. |
| 6,081,576 A | 6/2000 | Schanen et al. |
| 6,198,791 B1 | 3/2001 | He et al. |
| 6,246,743 B1 | 6/2001 | Kopp, III et al. |
| 6,295,331 B1 * | 9/2001 | Hsieh .......................... 378/19 |
| 6,310,938 B1 * | 10/2001 | Toth et al. ................... 378/147 |
| 6,327,329 B1 * | 12/2001 | Bromberg et al. ............ 378/19 |
| 2002/0021785 A1 * | 2/2002 | Toth et al. ................... 378/147 |

* cited by examiner

Primary Examiner—David V. Bruce
(74) Attorney, Agent, or Firm—Carl B. Horton, Esq.; Armstrong Teasdale LLP

(57) ABSTRACT

A CT imaging system and method are provided in which groups of adjacent detector elements of a detector array are ganged in an x-direction; and an object is scanned using the ganged groups of adjacent detector elements to acquire projection data. In one embodiment, to reduce degradation of images resulting from the ganged detector elements, an image of the object is reconstructed utilizing the acquired projection data and an adjusted iso-channel of the multislice detector array different from an iso-channel defined for scans performed without utilizing ganged groups of detector elements.

32 Claims, 8 Drawing Sheets

METHODS AND APPARATUS FOR COMPENSATING COMPUTED TOMOGRAPHIC CHANNEL GANGING ARTIFACTS

BACKGROUND OF THE INVENTION

This invention relates generally to methods and apparatus for computed tomographic (CT) imaging and other scanning imaging systems, and more particularly, to methods and apparatus for decreasing image artifacts and for retaining spatial resolution in systems providing increased volume coverage with limited data acquisition hardware.

To reduce the total scan time required for multiple slices, a "helical" scan may be performed. To perform a "helical" scan, the patient is moved in a z-axis direction synchronously with the rotation of the gantry, while the data for the prescribed number of slices is acquired. Such a system generates a single helix from a fan beam helical scan.

In at least one known CT imaging system, the detector array is segmented into a plurality of rows of detector elements, each row extending in an x-direction and defining an x-y "slice" out of a volume. Such imaging systems can acquire and process a plurality of slices of projection data to construct a plurality of images. Each of the reconstructed images corresponds to a different slice though the volume. Such CT imaging systems are referred to as "multislice" systems. Multislice systems provide more data available for reconstructing an image. In one exemplary embodiment of a multislice imaging system, N rows, e.g., N slices, of projection data are acquired for each view angle.

At least one known CT imaging system utilizes a detector array and a "data acquisition system" (DAS) for collecting image data. The detector array includes detector elements that individually produce an analog intensity signal representing impinging x-ray energy. The analog signals are then converted by the DAS to digital signals, which are used to produce image data.

In many applications of CT imaging systems such as cardiac imaging, it is desirable to increase the volume of an object imaged during a gantry rotation. One method for increasing imaging volume is to increase z-axis detector coverage, for example, by increasing the number of detector rows. To accommodate a larger number of detector rows without substantially increasing the size and complexity of the DAS, adjacent groups of detector elements in a detector row can be ganged. "Ganging groups of detector elements" (also called "ganging detector channels") refers to combining outputs of more than one detector cell adjacent one another in the x-direction. A detector having ganged detector elements requires less bandwidth than the same size detector array having separate detector outputs. Each ganged group of detector elements produces an output that requires only a communication path or channel through the DAS equivalent to that required by a single, unganged detector output. For example, a ganged group of detector elements produces data that can be sent via one multiplexed data slot position. Spare detector channels of the DAS can then be used to increase the number of detector rows from which data is acquired. When increased volume coverage is not needed, the channels and detector elements can be "unganged" or used individually. In this mode, the DAS accommodates the same amount of data, but processes fewer detector rows, so that less z-axis coverage is provided.

Ganging of adjacent detector elements in a detector row allows a hardware-limited imaging system to provide increased volume coverage. However, computer simulations of phantom scans has shown that ganging of detector elements in this manner results in a significant loss of spatial resolution and in increased aliasing artifact levels. Attempts to improve spatial resolution by boosting the image reconstruction kernel have resulted in worsened aliasing.

BRIEF SUMMARY OF THE INVENTION

There is therefore provided, in one embodiment of the present invention, a method for imaging an object with a scanning imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel (or "unganged iso-channel") of the multislice detector array when the scanning imaging system is utilized for scanning without ganging groups of detector elements. The method includes steps of ganging groups of adjacent detector elements in the x-direction; scanning an object with the scanning imaging system using the ganged groups of adjacent detector elements to acquire projection data; and reconstructing an image of the object utilizing the acquired projection data and an adjusted iso-channel of the multislice detector array different from the first iso-channel.

Another embodiment of the present invention provides a method for imaging an object with a computed tomography (CT) imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the CT imaging system is utilized for scanning without ganging groups of detector elements. The method includes: ganging groups of adjacent detector elements in the x-direction; scanning an object with the CT imaging system using the ganged groups of adjacent detector elements to acquire projection data; and reconstructing an image of the object utilizing the acquired projection data and an adjusted iso-channel of the multislice detector array different from the first iso-channel; wherein reconstructing an image of the object includes filtering and backprojecting the acquired projection data without interpolation.

Yet another embodiment of the present invention provides a method for imaging an object with a computed tomography (CT) imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the CT imaging system is utilized for scanning without ganging groups of detector elements. The method includes: ganging groups of adjacent detector elements in the x-direction; scanning an object with the CT imaging system using the ganged groups of adjacent detector elements to acquire projection data; and reconstructing an image of the object utilizing the acquired projection data and an adjusted iso-channel of the multislice detector array different from the first iso-channel, wherein the reconstructing includes performing a backprojection on the acquired projection data, and selecting, as the adjusted iso-channel, an iso-channel in the backprojection offset from the first iso-channel by an amount effective to reduce artifacts in the reconstructed image.

Still another embodiment of the present invention provides a method for imaging an object with a computed tomography (CT) imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the CT imaging system is utilized for scanning without ganging groups of detector elements. The method includes ganging groups of adjacent detector elements in the x-direction; scanning an object with the CT imaging system using the ganged groups of adjacent detector elements to acquire projection data; and reconstructing an image of the object utilizing the acquired projection data and an adjusted iso-channel of the multislice detector array different from the first iso-channel; wherein the reconstruction includes filtering the projection data utilizing a kernel having a cutoff frequency nearly twice a Nyquist spatial sampling frequency of said multislice detector array when said groups of detector elements are ganged.

In another aspect, the invention provides a scanning imaging system for imaging an object, the scanning imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the scanning imaging system is utilized for scanning without ganging groups of the detector elements, the scanning imaging system configured to:gang groups of adjacent the detector elements in the x-direction; scan the object using the ganged groups of the adjacent detector elements to acquire projection data; and reconstruct an image of the object utilizing the acquired projection data and an adjusted iso-channel of the multislice detector array different from the first iso-channel.

In still another aspect, the invention provides a computed tomographic (CT) imaging system for imaging an object, the CT imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the CT imaging system is utilized for scanning without ganging groups of the detector elements, the CT imaging system configured to: gang groups of adjacent the detector elements in the x-direction; scan the object using the ganged groups of adjacent detector elements to acquire projection data; and reconstruct an image of the object utilizing the acquired projection data and an adjusted iso-channel of the multislice detector array different from the first iso-channel; wherein to reconstruct the image of the object, the CT imaging system is configured to filter and backproject the acquired projection data without interpolation.

In yet another aspect, the present invention provides a CT imaging system for imaging an object, the CT imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the CT imaging system is utilized for scanning without ganging groups of the detector elements, the CT imaging system configured to: gang groups of adjacent the detector elements in the x-direction; scan the object using the ganged groups of adjacent detector elements to acquire projection data; and reconstruct an image of the object utilizing the acquired projection data and an adjusted iso-channel of the multislice detector array different from the first iso-channel; wherein to reconstruct the image of the object, the CT imaging system is configured to perform a backprojection on the acquired projection data, and to select, as the adjusted iso-channel, an iso-channel in the backprojection that is offset from the first iso-channel by an amount effective to reduce artifacts in the reconstructed image.

In yet another aspect, the present invention provides a CT imaging system for imaging an object, the CT imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the CT imaging system is utilized for scanning without ganging groups of the detector elements, the CT imaging system configured to: gang groups of adjacent the detector elements in the x-direction; scan the object using the ganged groups of adjacent detector elements to acquire projection data; and reconstruct an image of the object utilizing the acquired projection data and an adjusted iso-channel of the multislice detector array different from the first iso-channel; wherein to reconstruct the image, the CT imaging system is further configured to filter the acquired projection data utilizing a kernel having a cutoff frequency nearly twice a Nyquist spatial sampling frequency of the multislice detector array when the groups of detector elements are ganged.

Still another aspect of the present invention provides a processor configured to: input projection data representative of an object scanned with a scanning imaging system having ganged groups of adjacent detector elements; and reconstruct an image of the object utilizing the input projection data, wherein the reconstruction includes performing a backprojection on the acquired projection data, and selecting, as the adjusted iso-channel, an iso-channel in the backprojection offset from the first iso-channel by an amount effective to reduce artifacts in the reconstructed image.

Yet another aspect of the present invention provides a computer-readable medium having encoded thereon instructions configured to instruct a computer to: input projection data representative of an object scanned with a scanning imaging system having ganged groups of adjacent detector elements; and reconstruct an image of the object utilizing the input projection data, wherein the reconstruction includes performing a backprojection on the acquired projection data, and selecting, as the adjusted iso-channel, an iso-channel in the backprojection offset from the first iso-channel by an amount effective to reduce artifacts in the reconstructed image.

These embodiments of the present invention allow detector elements to be ganged to provide increased scan volumes, while reducing the degradation of images due to aliasing artifacts and reduced spatial resolution that would otherwise result from the ganging of detector elements.

DETAILED DESCRIPTION OF THE INVENTION

Figure 1:
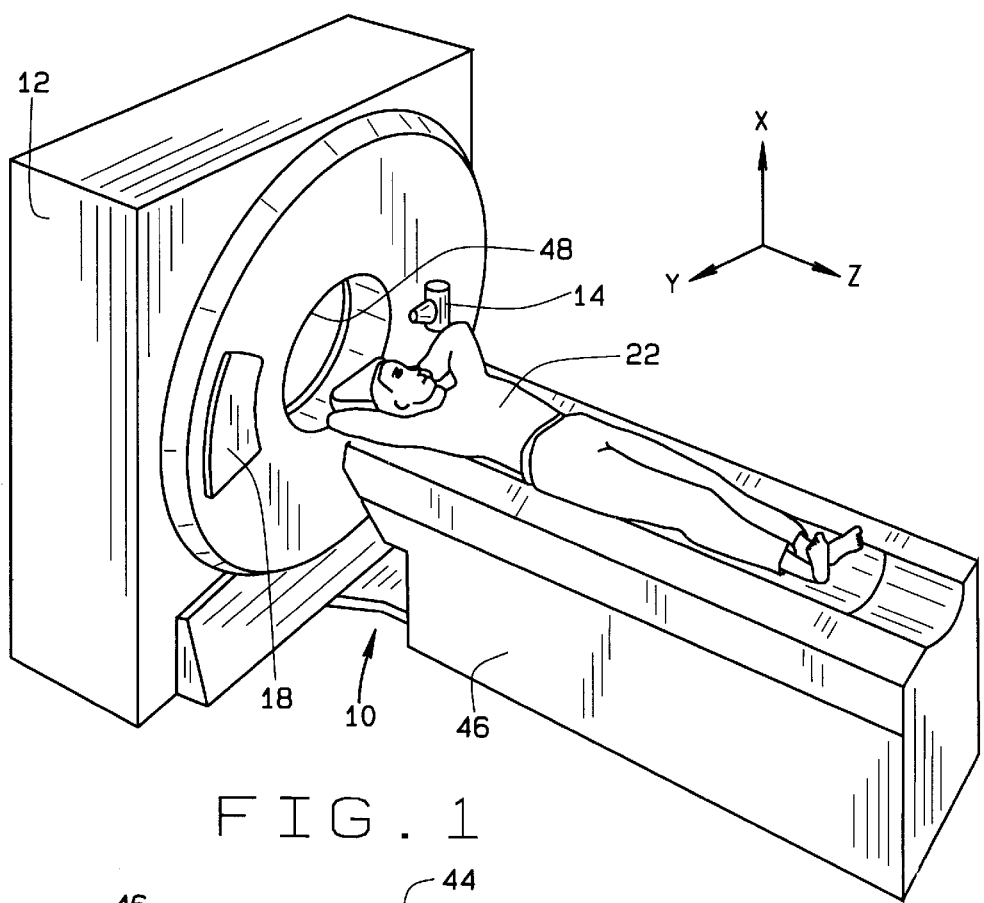
FIG. 1 is a pictorial view of a CT imaging system.
Figure 2:
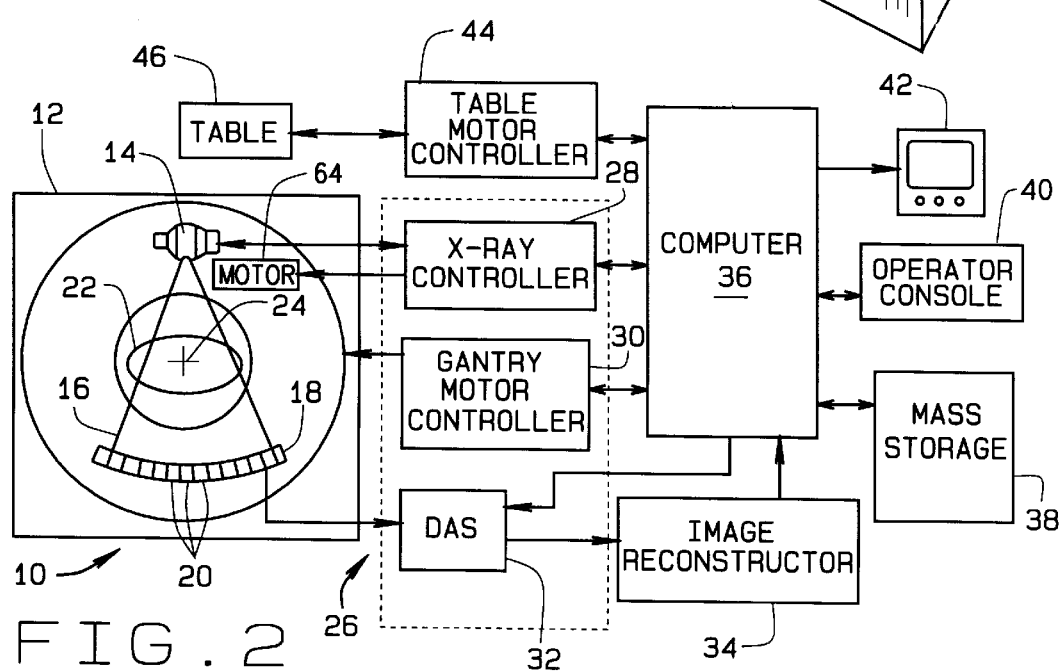
FIG. 2 is a block schematic diagram of the system illustrated in FIG. 1.

Referring to FIGS. 1 and 2, a scanning imaging system, represented by computed tomography (CT) imaging system 10, is shown including a rotating gantry 12 representative of a "third generation" CT scanner. An x-ray source 14 (e.g., an x-ray tube) on rotating gantry 12 emits a fan-shaped beam of x-rays 16 in an x-y plane toward a detector array 18 on the opposite side of gantry 12. Detector array 18 (often referred to simply as a "detector"), also on rotating gantry 12, is formed by detector elements or cells 20 that together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. Detector array 18 is a multislice detector array having detector elements 20 arranged in parallel rows, only one of which is shown in FIG. 2. The parallel rows extend in and define an x-direction. Thus, projection data corresponding to a plurality of parallel slices can be acquired simultaneously during a scan. When increased z-axis coverage (and thus, volume coverage) is desired during a scan, outputs from pairs of adjacent detector elements 20 are electrically combined to produce a single output signal per combined pair or detector element outputs.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. Each digital signal representing a detector output is transmitted by DAS 32 to image reconstructor 34, which receives the sampled and digitized x-ray data via separate channels and performs high speed image reconstruction. In one embodiment, each channel corresponds to a recurring time slot in one of a plurality of multiplexed signal paths. The reconstructed image is applied as an input to a computer 36 that stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 in gantry 12. Particularly, table 46 moves portions of patient 22 through gantry opening 48.

When increased z-axis coverage is desired, outputs from combined pairs of detector elements 20 are ganged. By rearranging electrical connections in DAS 32, the same number of DAS 32 channels can process data from a greater number of detector 18 rows because the ganging of detector element 20 outputs results in fewer signals being produced per detector 18 row.

In one embodiment of the present invention, imaging system 10 is configured to perform axial scans. In another embodiment, imaging system 10 is configured to perform helical scans. In one embodiment, imaging system 10 is selectively configurable to perform either an axial or a helical scan.

In one embodiment of the present invention, a quarter-quarter offset (also known as a detector quarter offset or "QQ") is used to double the sampling density and an image reconstruction algorithm having a kernel (a "standard reconstruction kernel") with a cut-off frequency of half of the Nyquist spatial sampling rate is used to process the double density data. An "iso-center" of CT imaging system 10 is defined as the center of rotation 24 of gantry 12. An 18 "iso-channel" is defined by an intersection of detector 18 with a straight line passing through the iso-center and a focal spot of x-ray beam 16. To combat aliasing, a location of a center detector element 20 of detector array 18 is offset by ¼ of the detector element 20 width to the iso-channel.

Figure 3:
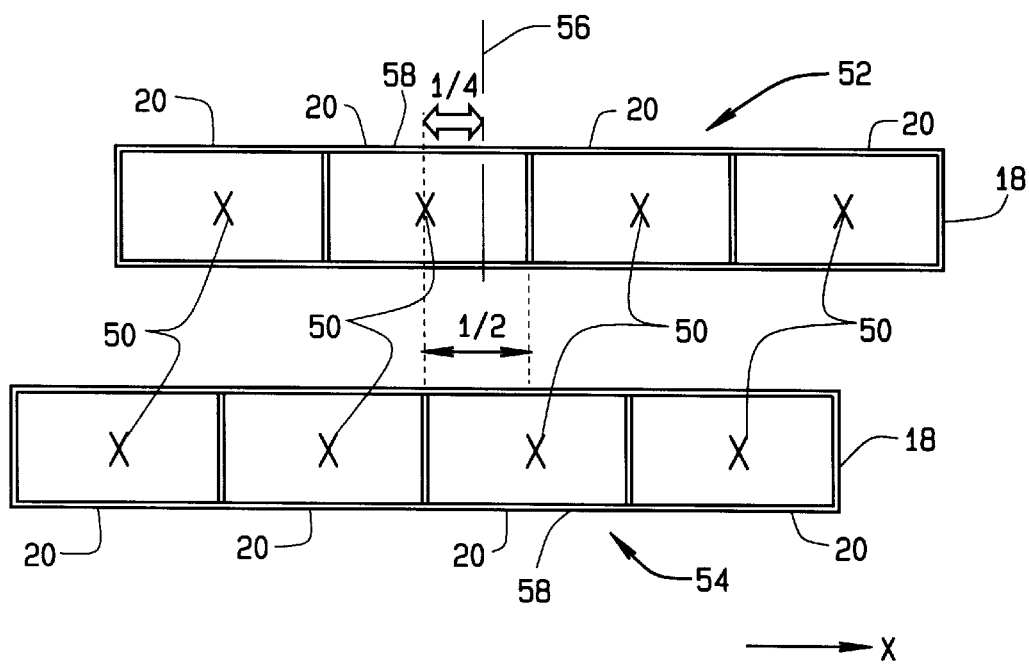
FIG. 3 illustrates a quarter-quarter offset in the x-direction for unganged detector elements in a single row of the detector array shown in FIGS. 1 and 2.

FIG. 3 is a representation of quarter-quarter offset for unganged detector elements 20 of a single row of detector array 18. FIG. 3 shows four detector elements 20 in a single row at the center of detector 18. Detector elements 20 are shown at a first position (top row) 52 at 0° gantry rotation and at a second position (bottom row) 54 at 180° gantry rotation. An effective data channel position 50 of each detector element 20 is represented by "x" in the center of each element. Referring in particular to detector element 58, at 0° gantry rotation, iso-channel 56 is offset to the right by ¼ of the width of detector element 58 with respect to its effective data channel position. However, at 180° gantry rotation 54, each element 20 is offset by ½ of an element width. Thus, iso-channel 56, when scanning without ganging groups of detector elements, is offset by ¼ element width to the left of detector element 58. The distance between the detector element 58 positions between gantry angles 0° and 180° is one-half element width, which allows sampling at mid-position between two detector elements 20 and effectively doubles the sampling rate of a single projection.

Figure 4:
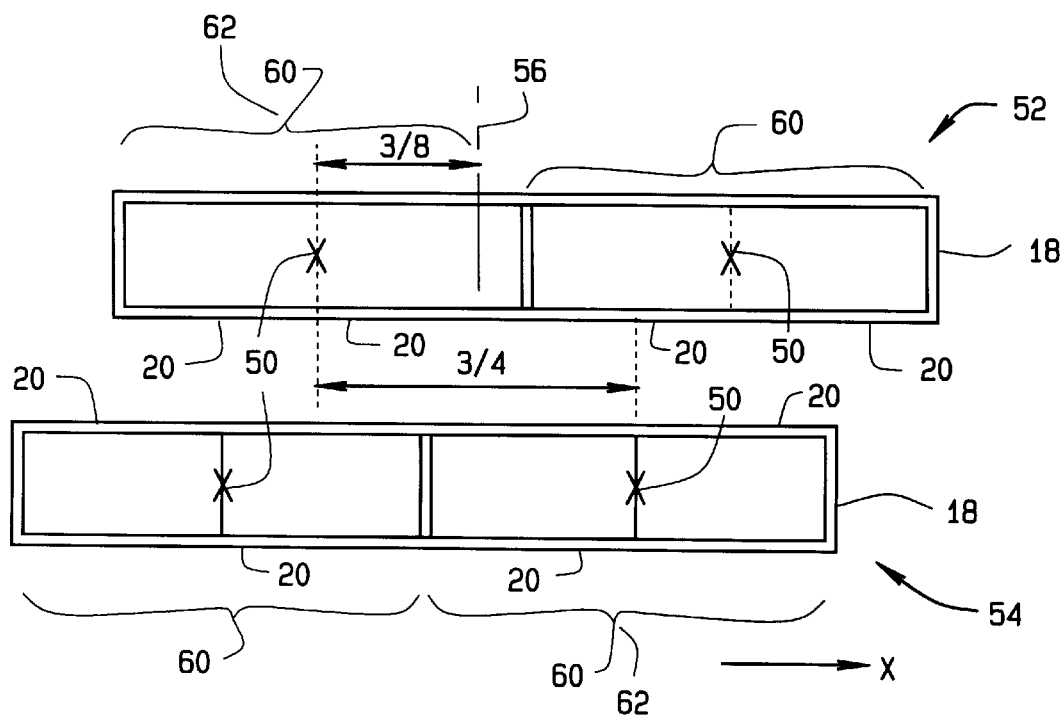
FIG. 4 is a representation of the detector elements of FIG. 3 shown ganged in the x-direction.

FIG. 4 is a representation of detector array 18 of FIG. 3 showing pairs 60 or groups of adjacent detector elements 20 ganged together in the x-direction, to increase a volume of an object 22 scanned to acquire projection data. As in FIG. 3, position 52 represents detector 18 in the 0° gantry rotation position and position 54 represents detector array 18 in the 180° gantry position. Effective sampling positions 50 for each paired combination 60 are now exactly halfway between individual elements 20. The distance of the closest paired combination 62 sampling position 50 to iso-channel 56 is now ⅜ of a paired combination 60 width. The 180° gantry position conjugate sample is now ¾ detector cell away from the previous position at 0° gantry position. Although two samples are still obtained within each paired combination width (one at each position 52, 54 for each combination 60), the second sample no longer straddles the previous sampling positions.

Figure 5:
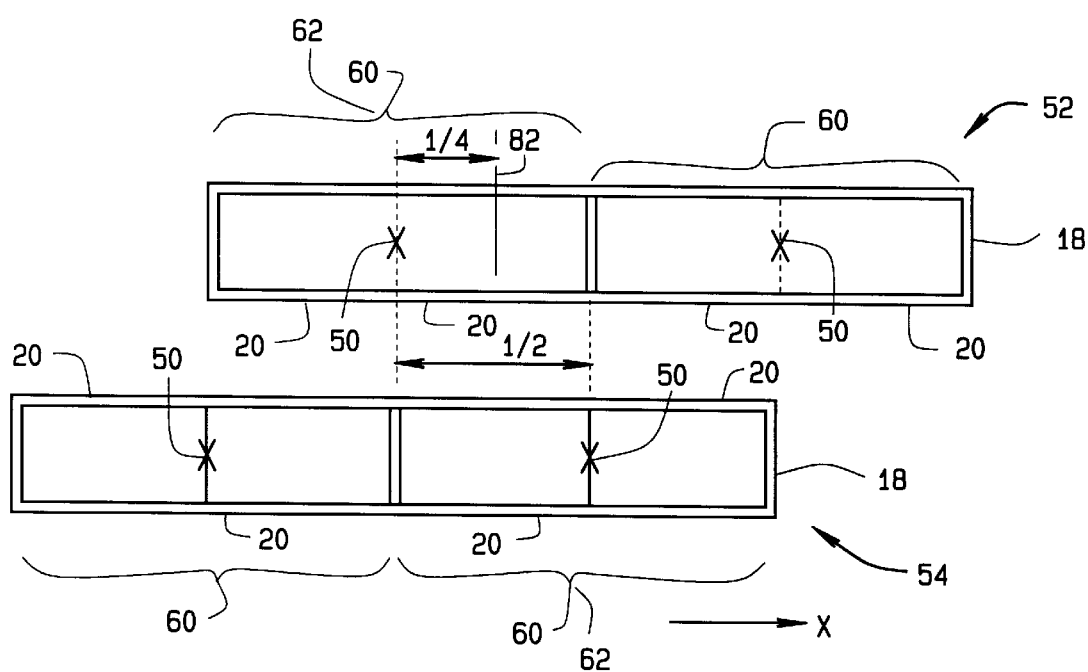
FIG. 5 is a representation of the ganged detector elements of FIG. 4 shown with a realigned iso-channel as used in one embodiment of the present invention.

In one embodiment of the present invention, to combat aliasing artifacts and to increase image resolution, detector iso-channel 56 is realigned or adjusted after cell ganging. In one embodiment, double-ganged detector elements are used for scanning with a quarter-quarter offset. Referring to FIG. 5, the focal spot of x-ray beam 16 is shifted or deflected so that a new iso-channel 82 is shifted ¼ detector element width. (This shift is relative the position of iso-channel 56 in FIG. 4.) In this embodiment, the offset distance between the conjugate samples is now ½ the width of a double-ganged group 60 of detector elements 20. An image of an object scanned with the ganged detector elements is reconstructed utilizing projection data acquired in the scan and the adjusted iso-channel 82, which is different from iso-channel 56 prior to ganging.

Iso-channel 56 is realigned to a new iso-channel 82 by x-ray focal spot deflection (e.g., magnetic or electrostatic deflection, such as in x-ray source tube 14 itself) or by a mechanical adjustment. In one embodiment employing mechanical adjustment, X-ray controller 26 includes additional components to control a motor 64 mechanically coupled to x-ray source 14, as shown in FIG. 2. The adjustment or realignment of iso-channel 56 is by an amount effect to reduce artifacts in the reconstructed image. In one embodiment, iso-channel 56 is shifted to a new iso-channel 82 by ⅛ of the width of a ganged group of detector elements. In one embodiment, rather than shifting x-ray source 14, an equivalent iso-channel adjustment is made by mechanically shifting detector 18.

For certain types of examinations, detector elements 20 can remain double-ganged during the entire examination. Therefore, there is no need to make dynamic adjustments of iso-channel 56 during these examinations. Focal spot deflection (or mechanical shift) is performed only once before the examination if needed, and once after the examination, if required for a subsequent examination or if it is desired to return the focal spot to a standard position after each examination.

Reconstructing an image of the object 22 utilizing acquired projection data and an adjusted iso-channel 82 of multislice detector array 18 different from a first iso-channel 56 is possible without physical adjustment of detector 18 and x-ray beam 16 configuration. In one embodiment, an original sampling configuration (for example, the configuration shown in FIG. 4) is kept. Rather than deflecting x-ray beam 16, an adjustment is made to effect an iso-channel adjustment in the backprojection to combat aliasing. A "virtual" adjusted iso-channel 82 results that is different from iso-channel 56. The adjustment is somewhat similar to adjustments used to effect an adjustment for a misaligned CT system 10. However, rather than assuming that the iso-channel is at an oppositely biased position during reconstruction as for adjustments of misaligned systems, the present invention sets a reconstruction iso-channel a fraction of the difference between the actual position 56 (as shown in FIG. 4) and an "ideal" position 82 (as shown in FIG. 5). Thus, the adjustment is made in an opposite direction from that which would be made were the adjustment made for misalignment rather than for alising correction. In one embodiment, a backprojection is performed on the acquired projection data utilizing an selected, adjusted iso-channel 82 offset from an unganged iso-channel of detector array 18. Adjusted iso-channel 82 is selected so as to be offset from the first, unganged iso-channel 56 by at least a portion of the distance between first iso-channel 56 and an iso-channel offset by ½ of the width of a double-ganged group 60 of detector elements 20. In another embodiment, a backprojection is performed on acquired projection data, and the iso-channel of the detector array is adjusted in the backprojection by an amount effective to reduce artifacts in the resulting image.

Figure 6:
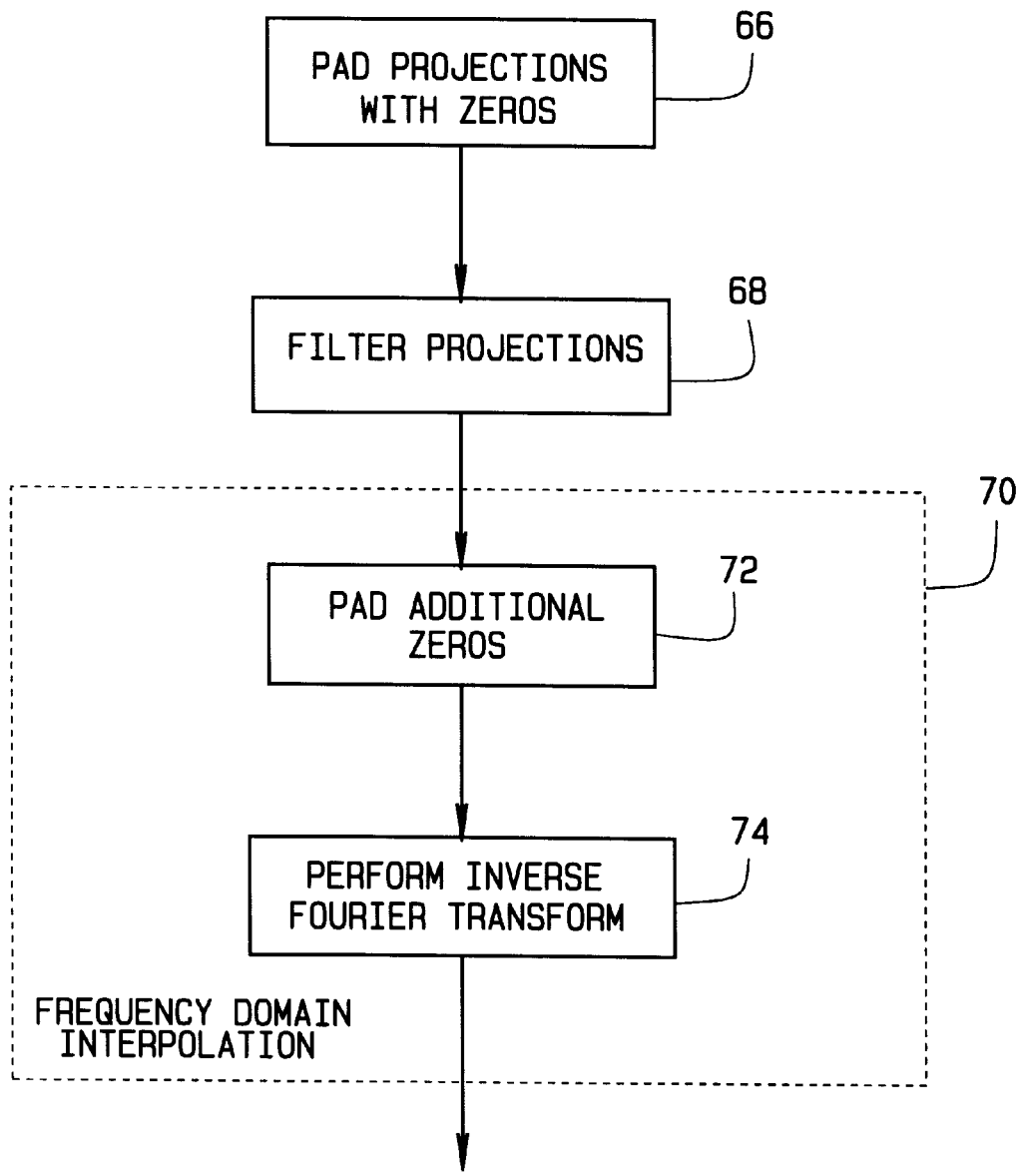
FIG. 6 i s a flow chart of filtering as practiced in one embodiment of the present invention.

It is desirable to minimize the effect of iso-channel 56 adjustment on spatial resolution and to reduce the number of mathematical operations required. Therefore, in one embodiment of the present invention and referring to FIG. 6, no interpolation is performed prior to filtering, so that filtering is performed on uninterpolated projection data. The ganged-cell projections are padded with zeros 66 to avoid inter-period interference and then filtered 68 with a kernel having a cutoff frequency nearly twice the Nyquist spatial sampling frequency of the ganged detector. By "nearly twice," it is meant that the cutoff frequency is between 1.6 and 2.0 times the Nyquist spatial sampling frequency. For example, in one embodiment, the cutoff frequency is 1.8 times the Nyquist spatial sampling frequency. Frequency domain interpolation 70 is then performed during the filtering step by padding more zeros 72 to the filtered projections prior to performing an inverse-Fourier transform 74.

Figure 7:
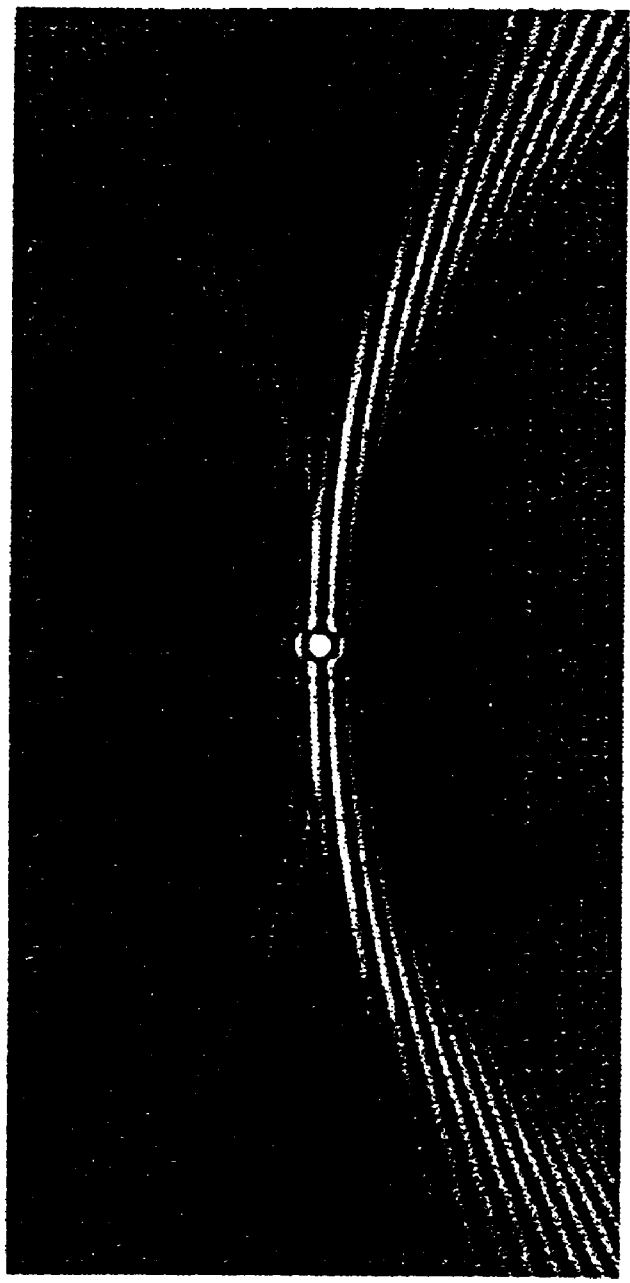
FIG. 7 is an image resulting from a computer simulation of the imaging of a dense wire with double-ganged detector elements, without iso-channel adjustment.

A computer simulation was used to test the effectiveness of the present invention. For this study, simulated scans of a dense wire 0.2 mm in diameter were simulated, assuming the scanning geometry of General Electric Medical Systems, Inc. CT/i Imaging System. FIG. 7 shows the resulting reconstructed image of the thin wire using direct double channel ganging without adjustment of the iso-channel. The cutoff frequency for the filter kernel is 1.8 times the Nyquist spatial frequency of the ganged cell. No polynomial boost was performed. A resulting aliasing artifact is clearly evident in the reconstructed image.

Figure 8:
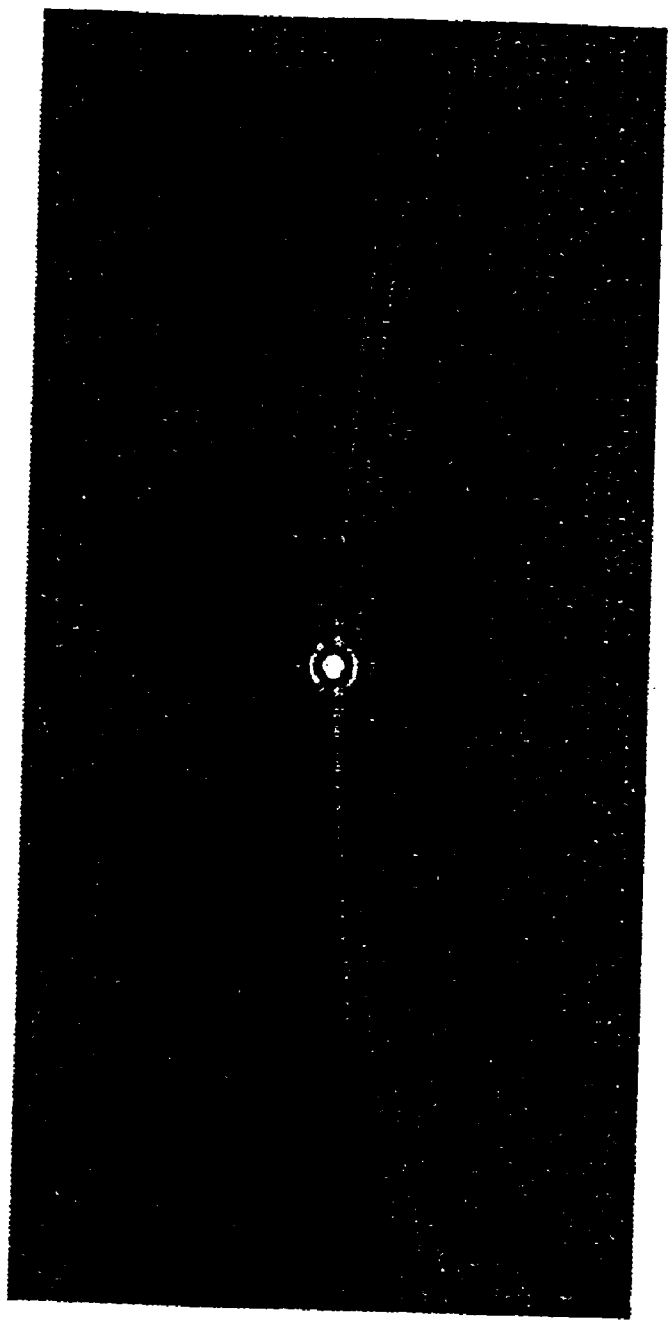
FIG. 8 is an image resulting from a computer simulation of the wire of FIG. 7 with double ganging and iso-channel adjustment.
Figure 10:
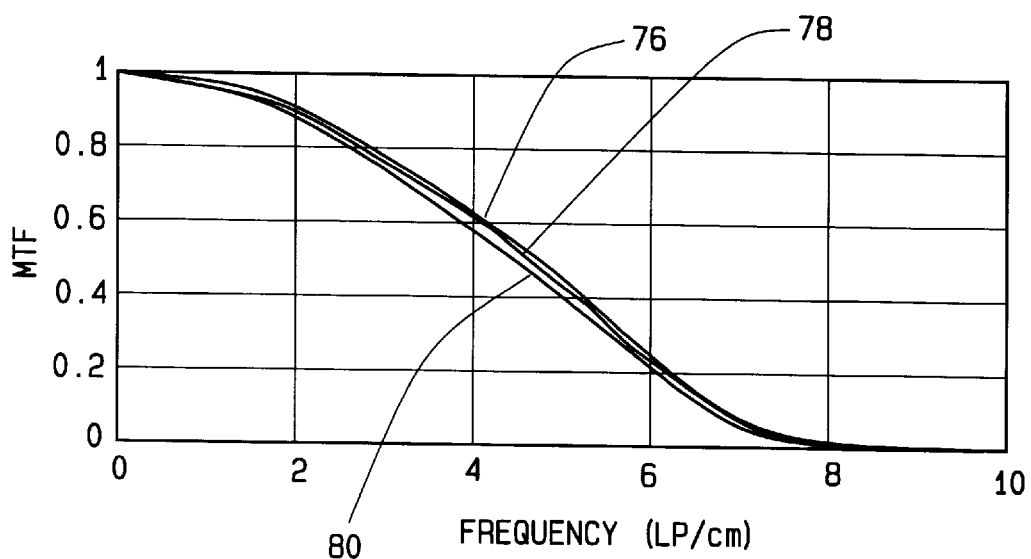
FIG. 10 is a graph of modulation transfer function (MTF) curves representing the reconstructed images shown in FIGS. 7, 8, and 9.

Next, a computer simulation was performed in which the x-ray focal spot was shifted by ¼ of a single cell width to enable double sampling. The reconstruction process was identical to the one used to produce FIG. 7. The resulting image, shown in FIG. 8, illustrates the reduction in aliasing artifacts that is achievable with embodiments of the present invention. An actual measurement of a wire using a CT/i Imaging System (available from General Electric Medical Systems, Inc., Milwaukee, Wis.) was performed to determine the effect of embodiments of the present invention on spatial resolution impact. The measured curves are shown in FIG. 10. Double-ganging without iso-channel readjustment is shown by a thick gray line 76, while double-ganging with realignment is shown by a solid line 78. Performance was found to be quite comparable.

Figure 9:
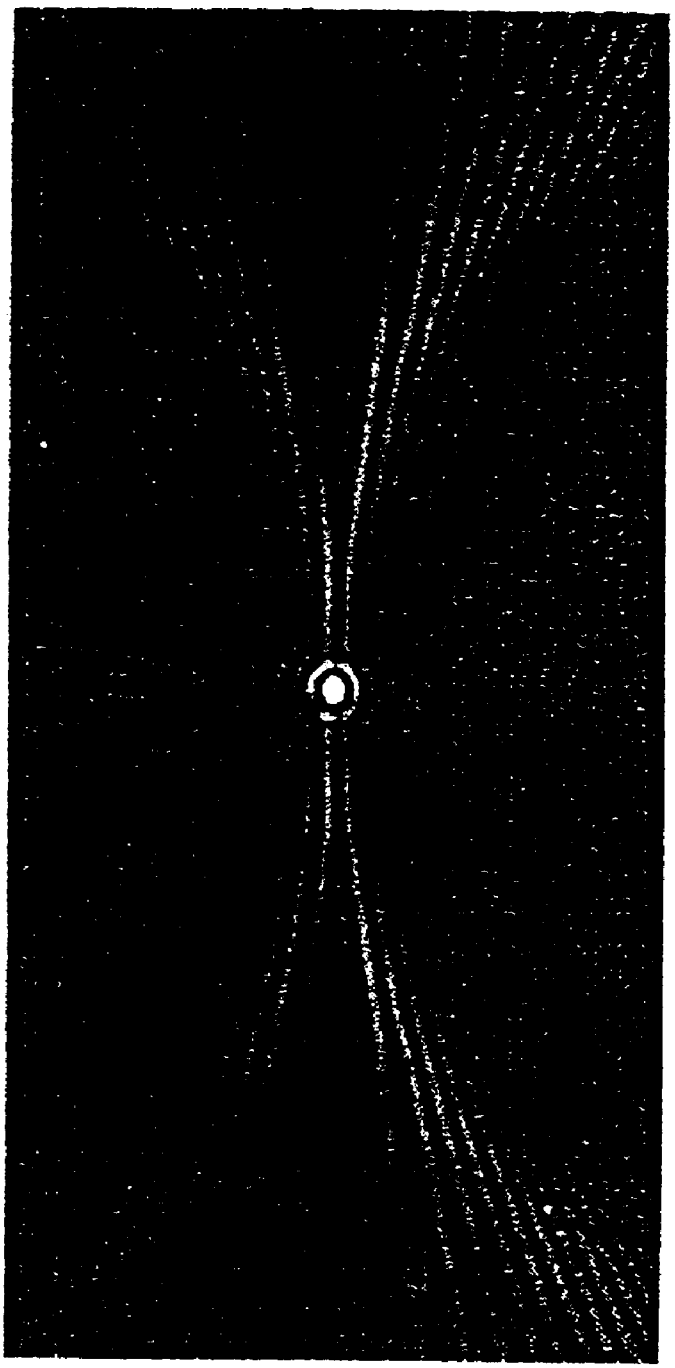
FIG. 9 is an image resulting from a computer simulation of the wire of FIG. 7 with double ganging and iso-channel shift in reconstruction.

Next, a computer simulation was performed to show the effect of introducing an iso-channel bias. In this simulation, the iso-channel for the backprojection was moved by ⅛ of a detector cell. As shown in FIG. 9, aliasing artifacts are significantly reduced as compared to FIG. 7, although the artifact is somewhat higher than FIG. 8. Referring to FIG. 10, an actual measurement of a wire (dotted line 80) shows a slight loss of spatial resolution.

Quantitative results are tabulated in Table I.

TABLE 1

MEASUREMENT RESULTS

|  | 50% MTF (LP/cm) | 10% MTF (LP/cm) |
|---|---|---|
| Double ganging with iso-channel shift in reconstruction | 4.53 | 6.83 |
| Double ganging without iso-channel shift in reconstruction | 4.75 | 6.85 |
| Double ganging with iso-channel adjustment | 4.80 | 6.87 |

In one embodiment of the present invention, imaging system 10 itself is configured as herein described utilizing a combination of hardware, software and/or firmware. However, in another embodiment, reconstruction of projection data is performed by a processor separate from scanning imaging system 10 using data acquired earlier by imaging system 10. The separate processor is, for example, a computer or workstation. In embodiments in which the computer or workstation includes a media reader, a machine-readable medium is provided that is encoded with instructions that instruct the computer or workstation to read the projection data and to reconstruct images therefrom. The computer readable medium is, for example, a CD-ROM a floppy diskette, or a digital magnetic tape.

It is thus apparent that embodiments of the present invention are effective in reducing aliasing artifacts and in increasing resolution when detector elements are ganged in the x-direction.

Those skilled in the art will recognize that the indefinite articles "a" or "an" preceding an element or step in the description or claims presented herein refer to one or more of the named elements or steps, unless such meaning is explicitly excluded. In addition, features described in connection with "one embodiment of the present invention," should not be understood as implying that those features may not be found in additional embodiments of the present invention.

While the invention has been described in terms of various specific embodiments, those skilled in the art will recognize that the invention can be practiced with modification within the spirit and scope of the claims.

What is claimed is:

1. A method for imaging an object with a scanning imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the scanning imaging system is utilized for scanning without ganging groups of detector elements, said method comprising:
ganging groups of adjacent detector elements in the x-direction;
scanning an object with the scanning imaging system using the ganged groups of adjacent detector elements to acquire projection data; and
reconstructing an image of the object utilizing the acquired projection data and an adjusted iso-channel of the multislice detector array different from the first iso-channel.

2. A method in accordance with claim 1 wherein the scanning imaging system is a computed tomographic (CT) imaging system, the x-ray beam has a focal spot, and reconstructing the image of the object utilizing the acquired projection data and an adjusted iso-channel of the detector array further comprises deflecting a focal spot of the x-ray source by an amount effective to reduce artifacts in the reconstructed image.

3. A method in accordance with claim 2 wherein the focal spot is mechanically adjusted.

4. A method in accordance with claim 2 wherein the focal spot is electrostatically deflected.

5. A method in accordance with claim 2 wherein the focal spot is magnetically deflected.

6. A method in accordance with claim 1 wherein said scanning comprises scanning the object utilizing a quarter-quarter offset and the ganged groups are double-ganged detector elements.

7. A method in accordance with claim 6 wherein reconstructing an image of the object utilizing the acquired projection data and an adjusted iso-channel comprises selecting, as the adjusted iso-channel, an iso-channel for which conjugate samples are offset by ½ of the width of a double-ganged group of detector elements.

8. A method in accordance with claim 6 wherein reconstructing an image of the object utilizing the acquired projection data and an adjusted iso-channel further comprises performing a backprojection on the acquired projection data and selecting, as the adjusted iso-channel, an iso-channel offset from the first iso-channel at least a portion of the distance between the first iso-channel and an iso-channel offset by ½ of the width of a double-ganged group of detector elements.

9. A method for imaging an object with a computed tomography (CT) imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the CT imaging system is utilized for scanning without ganging groups of detector elements, said method comprising:
ganging groups of adjacent detector elements in the x-direction;

scanning an object with the CT imaging system using the ganged groups of adjacent detector elements to acquire projection data; and reconstructing an image of the object utilizing the acquired projection data and an adjusted iso-channel of the multislice detector array different from the first iso-channel;

wherein reconstructing an image of the object comprises filtering and backprojecting the acquired projection data without interpolation.

10. A method for imaging an object with a computed tomography (CT) imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the CT imaging system is utilized for scanning without ganging groups of detector elements, said method comprising:

ganging groups of adjacent detector elements in the x-direction;

scanning an object with the CT imaging system using the ganged groups of adjacent detector elements to acquire projection data; and reconstructing an image of the object utilizing the acquired projection data and an adjusted iso-channel of the multislice detector array different from the first iso-channel, wherein said reconstructing comprises performing a backprojection on the acquired projection data, and selecting, as the adjusted iso-channel, an iso-channel in the backprojection offset from the first iso-channel by an amount effective to reduce artifacts in the reconstructed image.

11. A method for imaging an object with a computed tomography (CT) imaging system having a rotating gantry, a multislice detector array on the rotating gantry having parallel rows of detector elements, the parallel rows defining an x-direction, and an x-ray source on the rotating gantry configured to emit a fan-shaped x-ray beam in an x-y plane through an object to be imaged and towards the multislice detector array, the multislice detector array and the fan-shaped beam together defining an first iso-channel of the multislice detector array when the CT imaging system is utilized for scanning without ganging groups of detector elements, said method comprising:

ganging groups of adjacent detector elements in the x-direction;

scanning an object with the CT imaging system using the ganged groups of adjacent detector elements to acquire projection data; and reconstructing an image of the object utilizing the acquired projection data and an adjusted iso-channel of the multislice detector array different from the first iso-channel;

wherein said reconstruction comprises filtering the projection data utilizing a kernel having a cutoff frequency nearly twice a Nyquist spatial sampling frequency of said multislice detector array when said groups of detector elements are ganged.

12. A method in accordance with claim 11 wherein said filtering is performed on uninterpolated projection data.

13. A method in accordance with claim 12 wherein reconstructing an image of the object further comprises padding the uninterpolated projection data with zeros and padding the filtered projection data prior to performing an inverse-Fourier transform on the filtered projection data.

14. A scanning imaging system for imaging an object, said scanning imaging system having a rotating gantry, a multislice detector array on said rotating gantry having parallel rows of detector elements, said parallel rows defining an x-direction, and an x-ray source on said rotating gantry configured to emit a fan-shaped x-ray beam in an x-y plane through an object to be imaged and towards said multislice detector array, said multislice detector array and said fan-shaped beam together defining an first iso-channel of said multislice detector array when said scanning imaging system is utilized for scanning without ganging groups of said detector elements, said scanning imaging system configured to:

gang groups of adjacent said detector elements in the x-direction;

scan the object using said ganged groups of said adjacent detector elements to acquire projection data; and reconstruct an image of the object utilizing said acquired projection data and an adjusted iso-channel of said multislice detector array different from said first iso-channel.

15. A scanning imaging system in accordance with claim 14 wherein said scanning imaging system is a computed tomographic (CT) imaging system, said x-ray beam has a focal spot, and to reconstruct said image of the object utilizing said acquired projection data and said adjusted iso-channel of said detector array, said scanning imaging system is further configured to deflect said focal spot of the x-ray source by an amount effective to reduce artifacts in said reconstructed image.

16. A scanning imaging system in accordance with claim 15 wherein said CT imaging system is configured to mechanically adjust said focal spot.

17. A scanning imaging system in accordance with claim 15 wherein said CT imaging system is configured to electrostatically deflect said focal spot.

18. A scanning imaging system in accordance with claim 15 wherein said CT imaging system is configured to magnetically deflect said focal spot.

19. A scanning imaging system in accordance with claim 14 wherein said scanning imaging system is a computed tomographic (CT) imaging system configured to scan the object utilizing a quarter-quarter offset and said ganged groups are double-ganged groups of said detector elements.

20. A scanning imaging system in accordance with claim 19 wherein to reconstruct an image of the object utilizing said acquired projection data and said adjusted iso-channel, said CT imaging system is configured to select, as said adjusted iso-channel, an iso-channel for which conjugate samples are offset by ½ of the width of one of said double-ganged groups of detector elements.

21. A scanning imaging system in accordance with claim 20 wherein to reconstruct an image of the object utilizing said acquired projection data and said adjusted iso-channel, said CT imaging system is further configured to perform a backprojection on said acquired projection data and to select, as said adjusted iso-channel, an iso-channel offset from said first iso-channel at least a portion of the distance between said first iso-channel and an iso-channel offset by ½ of a width of one of said double-ganged groups of detector elements.

22. A computed tomographic (CT) imaging system for imaging an object, said CT imaging system having a rotating gantry, a multislice detector array on said rotating gantry having parallel rows of detector elements, said parallel rows defining an x-direction, and an x-ray source on said rotating gantry configured to emit a fan-shaped x-ray beam in an x-y plane through an object to be imaged and towards said multislice detector array, said multislice detector array and said fan-shaped beam together defining an first iso-channel of said multislice detector array when the CT imaging system is utilized for scanning without ganging groups of said detector elements, said CT imaging system configured to:
gang groups of adjacent said detector elements in the x-direction;
scan the object using said ganged groups of adjacent detector elements to acquire projection data; and
reconstruct an image of the object utilizing said acquired projection data and an adjusted iso-channel of said multislice detector array different from said first iso-channel;
wherein to reconstruct said image of the object, said CT imaging system is configured to filter and back-project said acquired projection data without interpolation.

23. A computed tomographic (CT) imaging system for imaging an object, said CT imaging system having a rotating gantry, a multislice detector array on said rotating gantry having parallel rows of detector elements, said parallel rows defining an x-direction, and an x-ray source on said rotating gantry configured to emit a fan-shaped x-ray beam in an x-y plane through an object to be imaged and towards said multislice detector array, said multislice detector array and said fan-shaped beam together defining an first iso-channel of said multislice detector array when the CT imaging system is utilized for scanning without ganging groups of said detector elements, said CT imaging system configured to:
gang groups of adjacent said detector elements in the x-direction;
scan the object using said ganged groups of adjacent detector elements to acquire projection data; and
reconstruct an image of the object utilizing said acquired projection data and an adjusted iso-channel of said multislice detector array different from said first iso-channel; wherein to reconstruct the image of the object, said CT imaging system is configured to perform a backprojection on said acquired projection data, and to select, as said adjusted iso-channel, an iso-channel in said backprojection that is offset from said first iso-channel by an amount effective to reduce artifacts in said reconstructed image.

24. A computed tomographic (CT) imaging system for imaging an object, said CT imaging system having a rotating gantry, a multislice detector array on said rotating gantry having parallel rows of detector elements, said parallel rows defining an x-direction, and an x-ray source on said rotating gantry configured to emit a fan-shaped x-ray beam in an x-y plane through an object to be imaged and towards said multislice detector array, said multislice detector array and said fan-shaped beam together defining an first iso-channel of said multislice detector array when the CT imaging system is utilized for scanning without ganging groups of said detector elements, said CT imaging system configured to:
gang groups of adjacent said detector elements in the x-direction;
scan the object using said ganged groups of adjacent detector elements to acquire projection data; and
reconstruct an image of the object utilizing said acquired projection data and an adjusted iso-channel of said multislice detector array different from said first iso-channel;
wherein to reconstruct said image, said CT imaging system is further configured to filter said acquired projection data utilizing a kernel having a cutoff frequency nearly twice a Nyquist spatial sampling frequency of said multislice detector array when said groups of detector elements are ganged.

25. A CT imaging system in accordance with claim 24 configured to perform said filtering on uninterpolated projection data.

26. A CT imaging system in accordance with claim 25 wherein to reconstruct an image of the object, said CT imaging system is further configured to pad said uninterpolated projection data with zeros, to pad filtered projection data with zeros, and to perform an inverse-Fourier transform on the filtered projection data after said padding of said filtered projection data.

27. A processor configured to:
input projection data representative of an object scanned with a scanning imaging system having ganged groups of adjacent detector elements; and
reconstruct an image of the object utilizing the input projection data, wherein said reconstruction comprises performing a backprojection on the acquired projection data, and selecting, as the adjusted iso-channel, an iso-channel in the backprojection offset from the first iso-channel by an amount effective to reduce artifacts in the reconstructed image.

28. A processor in accordance with claim 27 wherein the scanning imaging system has a Nyquist spatial sampling frequency, and wherein to reconstruct the image of the object, said processor is configured to filter the input projection data utilizing a kernel having a cutoff frequency nearly twice a Nyquist spatial sampling frequency of the ganged groups of detector elements.

29. A processor in accordance with claim 28 wherein the input projection data is uninterpolated projection data, and wherein said processor is further configured to pad the filtered projection data prior to performing an inverse-Fourier transform on the filtered projection data.

30. A computer-readable medium having encoded thereon instructions configured to instruct a computer to:
input projection data representative of an object scanned with a scanning imaging system having ganged groups of adjacent detector elements; and
reconstruct an image of the object utilizing the input projection data, wherein said reconstruction comprises performing a backprojection on the acquired projection data, and selecting, as the adjusted iso-channel, an iso-channel in the backprojection offset from the first iso-channel by an amount effective to reduce artifacts in the reconstructed image.

31. A computer-readable medium in accordance with claim 30, wherein the scanning imaging system has a Nyquist spatial sampling frequency, and wherein to reconstruct the image of the object, said computer-readable medium has instructions encoded thereon configured to instruct the computer to filter the input projection data utilizing a kernel having a cutoff frequency nearly twice a Nyquist spatial sampling frequency of the ganged groups of detector elements.

32. A computer-readable medium in accordance with claim 31 wherein the input projection data is uninterpolated projection data, and wherein said computer-readable medium has instructions encoded thereon configured to instruct the computer to pad the filtered projection data prior to performing an inverse-Fourier transform on the filtered projection data.

* * * * *